United States Patent [19]

Hauenstein et al.

[11] Patent Number: 5,190,729

[45] Date of Patent: *Mar. 2, 1993

[54] LUMINESCENT OXYGEN SENSOR BASED ON A LANTHANIDE COMPLEX

[75] Inventors: Bennett L. Hauenstein, Andover; Raysna Picerno, Acton, both of Mass.; Harry G. Brittain, Maplewood, N.J.; James R. Nestor, Nashua, N.H.

[73] Assignee: C. R. Bard, Inc., Murray Hill, N.J.

[ * ] Notice: The portion of the term of this patent subsequent to Aug. 29, 2006 has been disclaimed.

[21] Appl. No.: 655,648

[22] Filed: Feb. 14, 1991

Related U.S. Application Data

[62] Division of Ser. No. 326,729, Mar. 21, 1989, abandoned, which is a division of Ser. No. 904,963, Sep. 8, 1986, Pat. No. 4,861,727.

[51] Int. Cl.$^5$ .............................................. G01N 21/64
[52] U.S. Cl. .................................. 422/91; 422/88; 422/98; 422/82.07
[58] Field of Search ..................... 422/56, 57, 55, 88, 422/91, 98, 82.07; 252/301.18, 408.1, 82.33

[56] References Cited

U.S. PATENT DOCUMENTS

| Re. 31,879 | 5/1985 | Lubbers et al. | 436/133 |
| 3,440,173 | 4/1969 | Hovey et al. | 252/301.2 |
| 3,484,380 | 12/1969 | Kleinerman | 252/301.2 |
| 3,612,866 | 8/1971 | Stevens | 250/71 |

FOREIGN PATENT DOCUMENTS

106086 5/1978 Fed. Rep. of Germany .
2132398A 7/1984 United Kingdom .

OTHER PUBLICATIONS

Prendergast et a., "Oxygen Quenching of Sensitized Terbium Luminescence in Complexes of Terbium with Small Organic Ligands and Proteins," J. of Biological Chemistry, vol. 258, No. 7, Apr. 10, 1983 pp. 4075–4078.
Heller et al., "Intermolecular Energy Transfer From Excited Organic Compounds to Rare-Earth Ions in Dilute Solutions," J. Chemical Physics, vol. 42, No. 3, Feb. 1, 1965.
Whan et al., "Luminescence Studies of Rare Earth Complexes: Benzoyl-Acetonate and Dibenzoylmethide Chelates," J. Molecular Spectroscopy 8, 315–327 (1962).
Peterson et al., "Fiber-Optic Probe for In Vivo Measurement of Oxygen Partial Pressure," Anal. Chem. 1984, 56, pp. 62–67.

*Primary Examiner*—Robert J. Warden
*Assistant Examiner*—Timothy M. Mahon
*Attorney, Agent, or Firm*—Wolf, Greenfield & Sacks

[57] ABSTRACT

An oxygen sensor is provided for determination of the partial pressure of oxygen. In one aspect, the invention consists of oxygen-quenchable luminescent lanthanide complexes for an oxygen sensor. The complexes are oxygen-quenchable even though immobilized in a solid matrix, such as a solid polymeric matrix, and preferably are terbium complexes of Schiff base or $\beta$-diketone ligands. Certain preferred processes are described for improving the oxygen sensitivity of the lanthanide complexes. In another aspect, the invention consists of a combination measuring and reference analyte sensor containing both quenchable and nonquenchable luminescent materials. The materials luminesce at different wavelengths and thus may be transmitted together down a single optical fiber and later discriminated by means of filters and separtely detected. In a third aspect, the invention consists of a low-noise phosphorescent analyte sensor employing a gatable detector. By use of an analyte-quenchable material having a relatively long-lived phosphorescence, a pulsed excitation source, and selectively coupling the detector after the excitation source is off and any short-lived background luminescence has ended, a low-noise output signal consisting of the long-lived phosphorescence is selectively detected and the concentration of the analyte determined therefrom. In a preferred embodiment, all aspects of the invention are combined to produce a miniature in vivo oxygen sensor for use in the narrow blood vessels of the body.

16 Claims, 4 Drawing Sheets

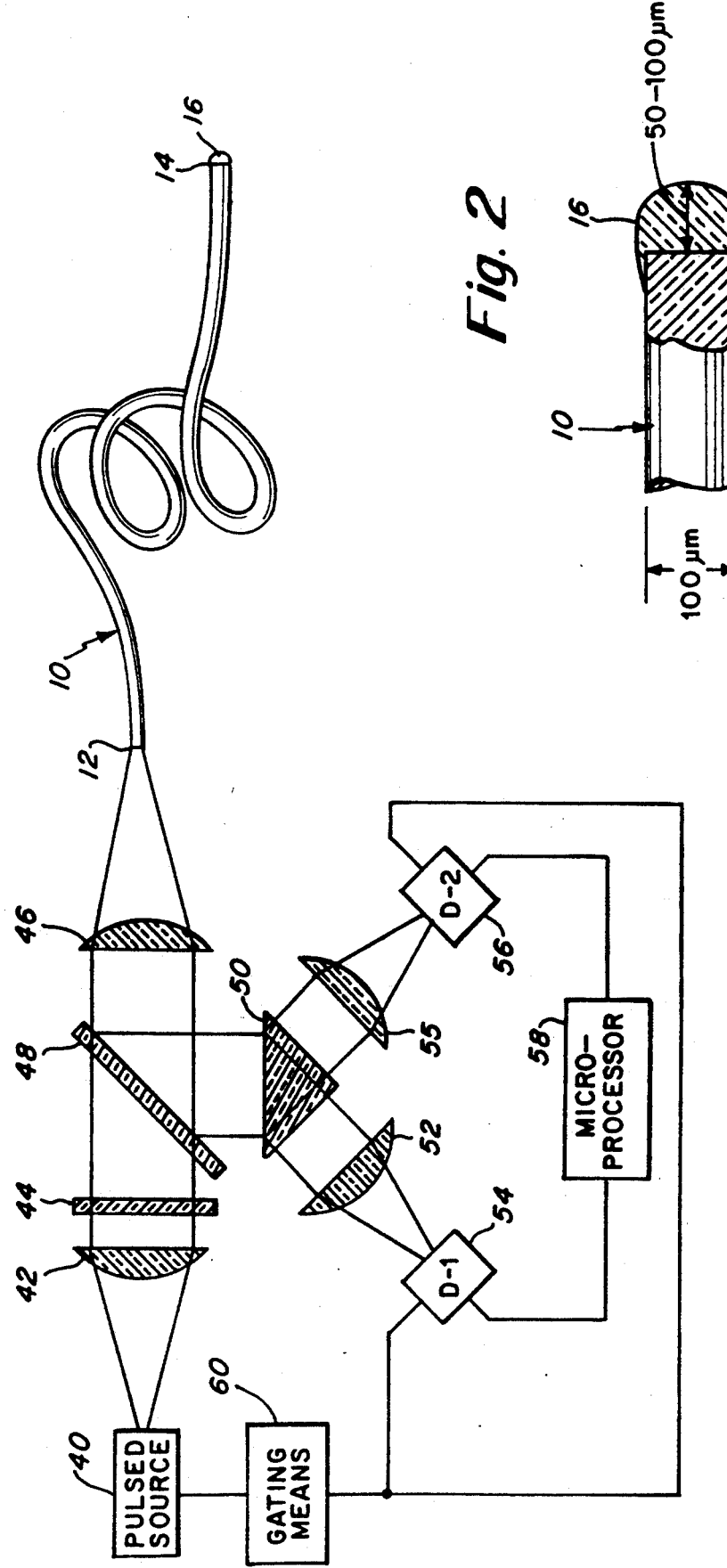

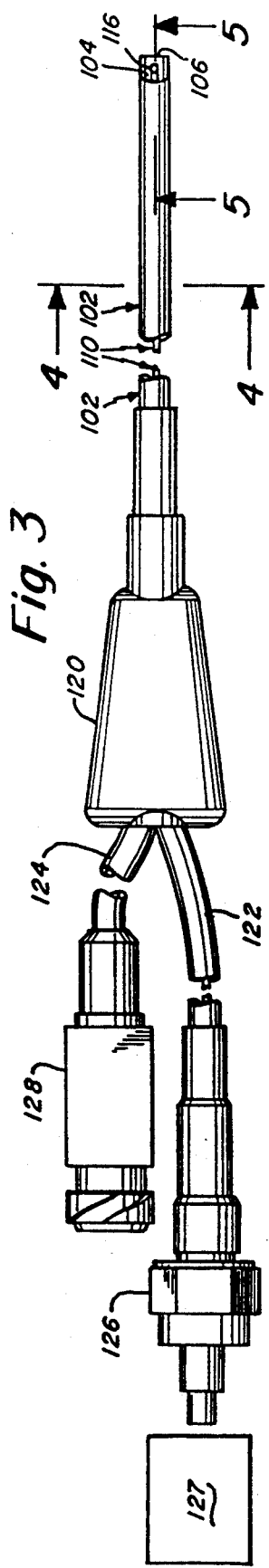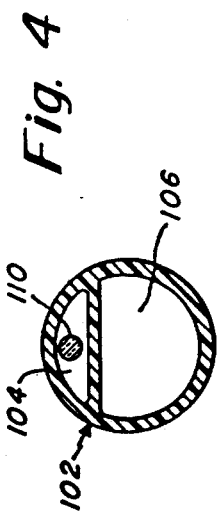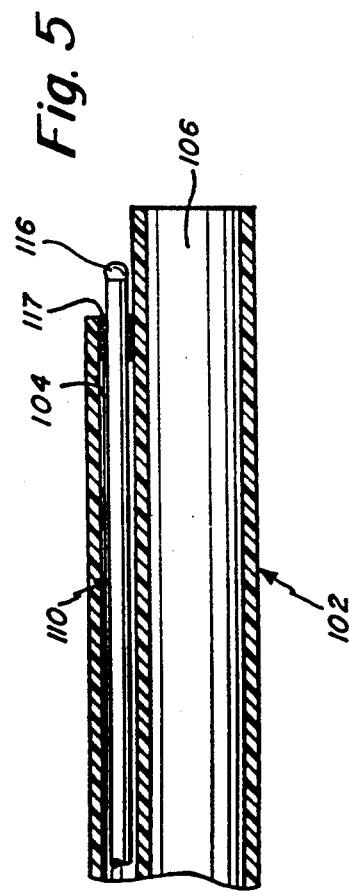

LUMINESCENT OXYGEN SENSOR BASED ON A LANTHANIDE COMPLEX

This application is a division of application Ser. No. 07/326,729, filed Mar. 21, 1989, now abandoned, which is a division of application Ser. No. 06/904,963, filed Sep. 8, 1986, now U.S. Pat. No. 4,861,727.

BACKGROUND OF THE INVENTION

This invention relates to sensors for detecting an analyte by luminescence quenching, and more particularly to oxygen-quenchable luminescent lanthanide complexes for an oxygen sensor, a combination measuring and reference analyte sensor containing both quenchable and nonquenchable luminescent materials, and a low-noise phosphorescent analyte sensor.

A blood gas analysis is performed on many hospital patients both during and after surgery. The three parameters of interest are the partial pressures of oxygen ($PO_2$) and carbon dioxide ($PCO_2$), and the negative logarithm of hydrogen ion activity, the pH. These three parameters give a good indication of a patient's cardiac, respiratory and circulatory functioning, and the rate of metabolism. Monitoring the level of oxygen gas in the blood is important for determining the amount of oxygen being delivered to the tissues.

Several sophisticated blood gas analyzers are commercially available for analyzing blood samples after the blood is extracted from the patient (in vitro). However, the withdrawal and subsequent analysis of a blood sample is both cumbersome and time-consuming and does not permit continuous monitoring of the dissolved gases in a patient's blood. There has been a need for many years for a system which would enable blood gas measurements to be made directly in the patient (in vivo), thereby avoiding the difficulties and expense inherent in the in vitro techniques.

Among the suggestions in the prior art was the use of indwelling electrode probes for continuous monitoring of the blood gas. The in vivo electrode probes have not been generally acceptable. Two principal disadvantages of electrode probes are the danger of using electrical currents in the body and the difficulty of properly calibrating the electrodes.

Also among the suggested techniques for in vivo measurement has been the use of fiber optic systems. In a fiber optic system, light from a suitable source travels along an optically conducting fiber to its distal end where it undergoes some change caused by interaction with a component of the medium in which the probe is inserted or interaction with a material contained in the probe tip which is sensitive to (i.e., modified by) a component in the medium. The modified light returns along the same or another fiber to a light-measuring instrument which interprets the return light signal.

Fiber optic sensors appear to offer several potential benefits. A fiber optic sensor is safe, involving no electrical currents in the body. Optical fibers are very small and flexible, allowing placement in the very small blood vessels of the heart. The materials used, i.e., plastic, metal, and glass, are suitable for long-term implantation. With fiber optic sensing, existing optical measurement techniques could be adapted to provide a highly localized measurement. Light intensity measurements could be processed for direct readout by standard analogue and digital circuitry or a microprocessor. However, although the potential benefits of an indwelling fiber optic sensor have long been recognized, they have not yet been realized in widely accepted commercial products. Among the principal difficulties has been in the development of a sensor in a sufficiently small size which is capable of relatively simple and economical manufacture so that it may be disposable.

An oxygen sensor based on oxygen-quenched fluorescence is described in U.S. Pat. Reissue No. 31,879 to Lübbers et al. Lëbbers et al. describe an optode consisting of a light-transmissive upper layer coupled to a light source, an oxygen-permeable lower diffusion membrane in contact with an oxygen-containing fluid, and a middle layer of an oxygen-quenchable fluorescent indicating substance, such as pyrenebutyric acid. When illuminated by a source light beam of a predetermined wavelength, the indicating substance emits a fluorescent beam of a wavelength different from the source beam and whose intensity is inversely proportional to the concentration of oxygen present. The resultant beam emanating from the optode, which includes both a portion of the source beam reflected from the optode and the fluorescent beam emitted by the indicating substance, is discriminated by means of a filter so that only the fluorescent beam is sent to the detector. In a second embodiment, the optode consists of a supporting foil made of a gas-diffusable material such as silicone in which the fluorescent indicating substance is randomly mixed, preferably in a polymerization type reaction, so that the indicating substance will not be washed away by the flow of blood over the optode. Lübbers et al. assert that both optodes can be adapted for in vivo use by disposing the same at the distal end of a catheter containing a pair of optical fibers for the incident and outgoing beams. However, the multi-layer optode of the first embodiment would be difficult to miniaturize. Lübbers et al. fails to disclose any method for attaching the alternative supporting foil to the distal end of the optical fibers or catheter. Furthermore, these sensors require at least two optical fibers which further limits miniaturization of the device.

Another $PO_2$ sensor probe utilizing an oxygen-sensitive fluorescent intermediate reagent is described in U.S. Pat. No. 4,476,870 to Peterson et al. The Peterson et al. probe includes two optical fibers ending in a jacket of porous polymer tubing. The tubing is packed with a fluorescent light-excitable dye adsorbed on a particulate polymeric support. The polymeric adsorbent is said to avoid the problem of humidity sensitivity found with inorganic adsorbents such as silica gel. The probe is calibrated by using a blue light illuminating signal and measuring both the intensity of the emitted fluorescent green signal and the intensity of the scattered blue illuminating signal. Again, it is difficult to miniaturize the Peterson et al. sensor tip wherein a porous particulate polymer is packed within an outer tubing.

U.S. Pat. No. 3,612,866 to Stevens describes another method of calibrating an oxygen-quenchable luminescent sensor. The Stevens device, designed for use outside the body, includes an oxygen-sensitive luminescent sensor made of pyrene and, disposed adjacent thereto, an oxygen-insensitive reference sensor also made of pyrene but which is covered with an oxygen-impermeable layer. The oxygen concentration is evaluated by comparing the outputs of the measuring and reference sensors.

A principal disadvantage of the prior art sensors is their large size which prohibits their use in the narrow blood vessels, such as the narrow vessels of the heart or those of neonates.

Another disadvantage with the prior art oxygen sensors is that the detected luminescence signal includes a great deal of background noise in addition to the oxygen-quenched luminescence. The noise consists of reflections of the incident signal and broadband luminescence generated by other components in the system, such as the optical fiber. It would be desirable to eliminate the background noise in order to obtain a more precise measurement of oxygen concentration.

It is known that lanthanide ions can be excited to luminescent levels through energy transfer from excited ligands complexing the ions. The ligand absorbs energy to reach an excited singlet state and then may undergo a radiationless transition to an excited triplet state. A transfer of energy from the ligand to the lanthanide ion can occur if the energy of the singlet or triplet state exceeds that of the luminescent state of the lanthanide ion.

Because of their narrow-line emissions, luminescent lanthanide complexes have found widespread use as laser materials, surface coatings, and as identifying probes in protein analysis. See U.S. Pat. Nos. 3,484,380 to Kleinerman, 3,440,173 to Hovey et al., and 4,037,172 to Filipescu et al. The lanthanide complexes have not been considered for use as oxygen sensors because they are not considered oxygen quenchable. In A. Heller et al. "Intermolecular Energy Transfer From Excited Organic Compounds To Rare Earth Ions In Dilute Solutions," 42 J. Chem. Physics 949–953 (Feb. 1965), it was found that noncomplexed aromatic aldehydes and ketones in solutions with lanthanide ions exhibited oxygen quenching. The authors state that quenching by oxygen was not readily observed with chelates of terbium and europium. While certain proteins and amino acid ligands useful in biological systems, such as 1-(p-methoxybenzyl)-EDTA, have exhibited some oxygen quenching of lanthanide luminescence in aqueous solution, the quenching was small, even in the presence of an oxygen saturated solution. Thus, it was not apparent that such compounds were sufficiently sensitive even in an agueous solution to produce a useable oxygen sensor, nor that such compounds immobilized in a solid matrix would exhibit any sensitivity at all. See F. Prendergast et al., "Oxygen Quenching Of Sensitized Terbium Luminescence In Complexes Of Terbium With Small Organic Ligands And Proteins," 258 J. Bio. Chem. 4075–4078 (1983); A. Abusaleh et al., "Excitation And De-Excitation Processes In Lanthanide Chelates Bearing Aromatic Sidechains," 39 Photochemistry and Photobiology 763–769 (1984).

It is a surprising aspect of this invention that certain lanthanide complexes have been found to be sufficiently oxygen quenchable for use as an oxygen sensor.

It is an object of this invention to provide oxygen-quenchable luminescent materials having very narrow emission bands for use as oxygen sensors.

Another object is to provide luminescent materials which are oxygen quenchable in solid form for use as oxygen sensors.

A further object is to provide methods of improving the oxygen sensitivy of the solid luminescent materials.

A further object is to provide oxygen-quenchable luminescent materials which can be excited at wavelengths above 300 nm and thus can be used with commercially-available optical fibers for constructing an in vivo oxygen probe.

Another object is to provide a combination measuring and reference analyte sensor containing both quenchable and nonquenchable luminescent materials.

A further object is to provide luminescent materials having a relatively long-lived luminescence or phosphorescence.

A still further object is to provide a low-noise oxygen sensor based on such phosphorescent materials.

Still another object is to provide a small diameter catheter containing a precalibrated, low-noise oxygen sensor for use in the narrow blood vessels of the body.

SUMMARY OF THE INVENTION

According to this invention, oxygen-quenchable luminescent lanthanide complexes are provided for use as oxygen sensors. The complexes exhibit significant oxygen sensitivity in both solid form and dissolved in solution. In a preferred embodiment, the sensor consists of a solid solution of the complex in a polymeric matrix. The complexes can be excited to luminesce using wavelengths above 300 nm and therefore can be used with commercially-available optical fibers which transmit above 300 nm to construct a fiber optic sensor probe positionable within the narrow blood vessels of the body. Furthermore, the complexes exhibit a long-lived luminescence or phosphorescence and thus are adapted for use in a low-noise phosphorescent oxygen sensor according to another aspect of this invention.

The lanthanide complexes of this invention consist of at least one lanthanide ion which emits a narrow-line luminescence from a predetermined energy state and at least one ligand having an excited ligand energy state from which it transfers energy to the lanthanide ion causing the ion to luminesce. It is believed that the excited ligand energy state is substantially equal to the predetermined energy state so that the lanthanide ion and ligand form a resonant pair between which energy is rapidly transferred back and forth. The prescence of oxygen either interferes with this energy transfer between the ligand and metal ion or quenches the liquid excited state and thus substantially quenches the luminescence of the complex.

A preferred oxygen-quenchable lanthanide complex of this invention consists of at least one terbium ion complexed with at least one Schiff base or $\beta$-diketone ligand. When exposed to ultra-violet or near visible radiation, the terbium complex emits a narrow-line luminescence having a relatively long lifetime of $10^{-5}$ seconds or longer. The complex when disposed in solid solution in a polymeric matrix exhibits significant oxygen sensitivity so as to permit the determination of $PO_2$ in the blood to an accuracy of greater than ±5%.

In another aspect, the oxygen-quenchable material preferably consists of a multi-metal ion lanthanide complex having a plurality of lanthanide metal ions and a plurality of ligands wherein at least one of the ligands is complexed with more than one of the lanthanide ions. For example, a lanthanide complex found to have significant oxygen sensitivity consists of three terbium ions and three Schiff base ligands. It is believed that each of the Schiff base ligands is complexed to more than one terbium ion and thus a resonance is established between each ligand and more than one terbium ion. The complex is believed to form a ring structure which permits energy transfer from the three ligands forming the ring to any of the three terbium ions disposed on the ring. The multi-metal ion complex has been found to have enhanced oxygen sensitivity.

In a preferred embodiment, the oxygen sensor of this invention consists of the lanthanide complex in solid solution in an oxygen-permeable solid polymeric matrix. The sensor may then be placed directly in a fluid sample and the oxygen molecules from the fluid will diffuse into the matrix and contact the lanthanide complex. The polymeric matrix should be transparent to and not degraded by radiation at the wavelength which excites the lanthanide complex and at the wavelength of the luminescent radiation emitted by the lanthanide complex. It is further preferred to provide a polymeric matrix which will adhesively bind directly to an optical fiber so as to conveniently position the sensor at the distal end of the fiber, as by dipping the fiber tip in a solution of the polymer and complex.

The invention further includes a method of improving the oxygen sensitivity of a lanthanide complex by deprotonating the ligand with a strong base such as hydroxide before complexing the ligand and lanthanide ion. Furthermore, by complexing the ligand and ion in an hydroxide solution, it is believed that hydroxide groups will coordinate with more than one lanthanide ion to create multi-metal ion complexes.

Another process of this invention for making a solid lanthanide complex having improved oxygen sensitivity consists of a purification step wherein non-oxygen sensitive byproducts are removed. The process consists of dissolving the lanthanide complex in a suitable organic solvent, such as chloroform or ethanol, removing the non-oxygen sensitive byproducts, and reprecipitating the lanthanide complex to produce a compound which is more oxygen sensitive.

In another aspect of this invention, a precalibrated luminescent analyte sensor is provided consisting of a quenchable luminescent measuring material having a luminescence in a first wavelength range which is quenched by the analyte, and a non-quenchable luminescent reference material disposed adjacent to the quenchable luminescent material and having a luminescence in a second wavelength range different from the first range and which is not substantially quenched by the analyte. The luminescence from the second material, which is not quenched by the analyte, acts as a reference signal for detecting changes in the optical system or source means while the sensor is in use. A single optical fiber can be used with this sensor because the luminescence signals from the first and second materials are at different wavelengths and thus can be separated by filters and individually measured. Preferably, the first and second materials are disposed in solid solution in a polymeric matrix which is permeable to the analyte, not degraded by the incident or luminescence energy signals, and disposed at the distal end of the fiber. The sensor tip can be prepared by dipping the fiber end in a solution of the polymer and luminescent materials and evaporating the solvent to form a polymeric bead. Thus, a very small diameter sensor probe can be made based on a single fiber having a small polymeric bead at its distal end as the sensor.

In another aspect of this invention, an analyte sensor is provided based upon a long-lived luminescent or phosphorescent measuring material whereby short-lived emissions in the system are discriminated against to produce a relatively low-noise output signal. The sensor includes a quenchable phosphorescent material having a relatively long-lived luminescence that is quenched by the analyte of interest, source means for generating a pulsed incident energy signal to excite the phosphorescent material, detector means coupled to the phosphorescent material for detecting the long-lived luminescence, and means for selectively coupling and decoupling the detector and phosphorescent material so that the detector is coupled only when the source means is off and any short-lived background luminescence generated in the system has substantially ended so that the detector receives an output luminescent signal composed of substantially only the long-lived luminescence from the phosphorescent material. This system is particularly adapted for an in vivo sensor because it produces a low-noise output signal with only a single optical fiber coupling the phosphorescent material to both the source and detector, and thus the sensor can be made very small. The lanthanide oxygen-quenchable complexes of this invention have a sufficiently long lifetime to permit the construction of such an in vivo phosphorescent oxygen sensor.

BRIEF DESCRIPTION OF THE DRAWINGS

FIG. 1 is a schematic illustration of the fiber optic oxygen sensor of this invention and associated instrumentation.

FIG. 2 is a partial sectional view of the distal end of the fiber optic sensor.

FIG. 3 is a fragmented illustration of a catheter embodying the fiber optic sensor.

FIG. 4 is a cross-sectional view taken along section lines 4—4 of FIG. 3 showing the catheter lumens.

FIG. 5 is a cross-sectional view taken along section lines 5—5 of FIG. 3 showing the distal end of the catheter.

DETAILED DESCRIPTION OF THE PREFERRED EMBODIMENTS

Figure 6:
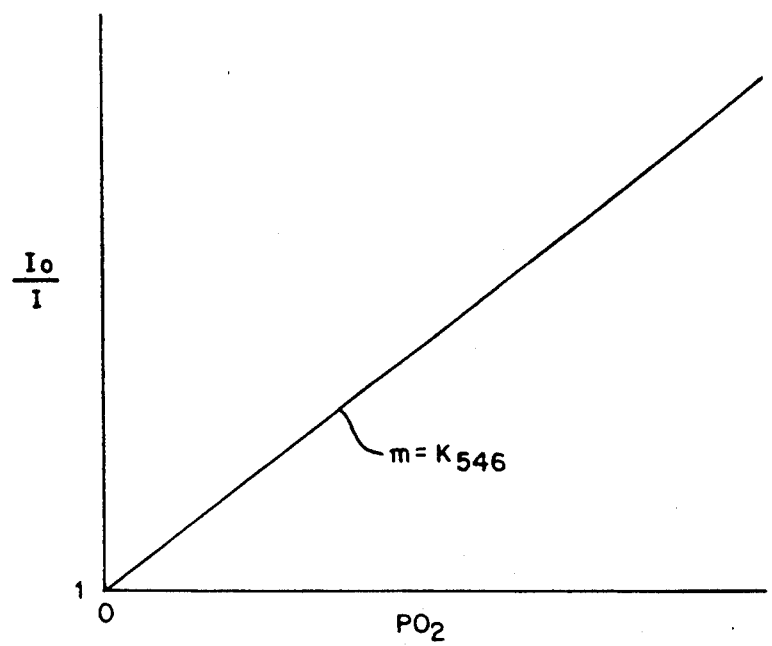
FIG. 6 is a graphical illustration of the Stern-Volmer relation for an oxygen sensitive terbium complex.

According to a first aspect of this invention, oxygen-quenchable luminescent lanthanide complexes are provided for use as oxygen sensors. The complexes exhibit sufficient oxygen sensitivity in both solid form and in solution for use as oxygen sensors. By complex it is meant a coordination compound formed by the union of a metal ion with a non-metallic ion or molecule called a ligand or complexing agent.

In the lanthanide complexes of this invention, the metal ion is an ion of a lanthanide element. The lanthanide elements, also known as the rare earth elements, consist of those elements having atomic numbers from 57 to 71, and thus include lanthanum, cerium, praseodymium, neodymium, promethium, samarium, europium, gadolinium, terbium, dysprosium, holmium, erbium, thulium, ytterbium, and lutetium. The lanthanide ions which exhibit a narrow-line luminescence are preferred, such as the +3 ions of samarium, europium, dysprosium, terbium, and neodymium.

The lanthanide ions are excited to luminesce by the transfer of energy from at least one ligand which is complexed to one or more lanthanide ions. The ligand absorbs energy to reach an excited singlet state, and may undergo a radiationless transition to an excited triplet state. A transfer of energy from the ligand to the lanthanide ion may occur if the energy of the singlet or triplet states exceeds that of the luminescent state of the lanthanide ion. The oxygen sensitivity of the lanthanide complexes of this invention is believed to result from the creation of a long-lived resonant state between the excited ligand and the excited lanthanide ion of the complex whereby energy is rapidly transferred back and forth between the ligand and ion, and wherein oxygen interferes with the transfer of energy so as to quench the luminescence of the complex.

It has been found that the luminescent lanthanide complexes of this invention are oxygen sensitive when the excited state energy of the ligand is substantially equal to the predetermined excited energy state of the lanthanide ion from which luminescence occurs. When these energies are substantially equal, the ion and ligand form a resonant pair between which energy is rapidly transfered back and forth. Oxygen gas interferes with the energy transfer between the resonant pair or absorbs the energy of the excited ligand to thereby reduce the luminescence intensity. When the excited ligand energy state and the predetermined excited energy state are close enough in energy, the lifetime of the ligand excited state is apparently lengthened through a resonance process with the lanthanide ion excited state. The result is a greater oxygen sensitivity because the oxygen has, in effect, more time in which to interfere with the transfer of energy between the resonant pair or absorb energy from the excited ligand to quench the luminescence.

It has been found that the terbium +3 ion forms oxygen-quenchable complexes with Schiff base ligands. The Schiff base ligand consists of at least one aldehyde or ketone and at least one primary amine. Preferably, the ligand is derived from salicylaldehyde or substituted salicylaldehyde, wherein the substituted salicylaldehyde contains groups other than hydrogen in the 3,4,5, and/or 6 positions. The groups may be halides, hydrocarbons, aldehydes, hydroxides, or any other group. Preferably, the primary amine is selected from the group consisting of 1-amino-2-propanol, 1-amino-2-butanol, 2-amino-1-phenyl-1,2-propanediol, ethylenediamine, and propylenediamine. Preferred Schiff base ligands include:

1:1 salicylaldehyde : 1-amino-2-propanol;
1:1 salicylaldehyde : 1-amino-2-butanol;
1:1 5-chloro-salicylaldehyde : 1 amino-2-propanol;
1:1 3,5-dichloro-salicylaldehyde : 1-amino-2-propanol;
1:1 salicylaldehyde : 2-amino-1-phenyl-1,2-propanediol;
2:1 salicylaldehyde : ethylenediamine;
2:1 salicylaldehyde : propylenediamine;
1:1 o-vanillin : 1-amino-2-propanol; and
1:1 m-vanillin : 1-amino-2-propanol.

Known methods for preparing Schiff base complexes can be used, such as those described in U.S. Pat. No. 3,484,380 to Kleinerman.

The terbium +3 ion also forms oxygen-quenchable complexes with $\beta$-diketone ligands. Preferred $\beta$-diketone ligands include:
benzoylacetone;
thenoyltrifluoroacetone;
trifluoroacetylacetone; and
furylbutanedione.

Known methods for preparing $\beta$-diketone complexes can be used, such as those described in R. E. Whan et al., "Luminescent Studies of Rare Earth Complexes: Benzoylacetonate and Dibenzoylmethide Chelates," 8 J. Mol. Spectroscopy 315-327 (1962).

These Schiff base and $\beta$-diketone terbium complexes are excitable by ultra-violet or visible radiation and emit a luminescent radiation at wavelengths longer than the excitation wavelength. All of these complexes can be excited above 300 nm, and preferably are excited at about 350-360 nm.

Furthermore, the lanthanide complexes of this invention can be a ternary (or higher) complex where in addition to a Schiff base and/or $\beta$-diketone ligand, an additional ligand is provided. The additional ligand acts as a filler to complete the coordination geometry and to give a stabler complex. Suitable additional ligands include polyaminocarboxylic acids and heterocyclic polycarboxylic acids such as ethylenediaminetetraacetic acid (EDTA), 1,2-diaminocyclohexane-N,N,N',N'-tetraacetic acid (CyDTA), diethylenetriaminepentaacetic acid (DTPA), ethylene glycol-bis(aminoethyl)-tetraacetic acid (EGTA), and dipicolinic acid (dpa).

It has been found that certain terbium complexes with Schiff base and $\beta$-diketone ligands are oxygen quenchable, while europium complexes with the same ligands are not. The oxygen sensitivity of the terbium complexes is believed to be due to the fact that the excited ligand energy state is substantially equal to the excited energy state of the terbium ion, whereas the excited ligand energy state is not substantially equal to the excited energy state of the europium ion and therefore the europium complex is not oxygen sensitive. By way of example, a preferred oxygen-sensitive terbium complex, hereinafter referred to as Tb(SALAPPD), is formed of three terbium +3 ions, three hydroxides, and three Schiff base ligands of the formula 1:1 salicylaldehyde : 2-amino-1-phenyl-1,2-propanesalicylald diol (SALAPPD). Each terbium ion has at least two binding sites and thus the ligands are chelates.

The complex is believed to have a closed ring structure with both the ligands and hydroxides acting as bridges. Each ligand is believed to be complexed to two lanthanide metal ions in the ring. The complex is thus a multi-metal complex and it is believed that energy transfer occurs between the various lanthanide metal ions and ligands on the ring. It is further believed that the hydroxide groups may act as bridges between the lanthanide metal ions in the complex.

The terbium ion has a $^5D_4$ excited state at about 490 nm (20,410 cm$^{-1}$). It has been found that the SALAPPD ligand has an excited energy state within about 10 nm (410 cm$^{-1}$) of the $^5D_4$ excited state of the terbium ion. The excited state of the Schiff base ligand is thus sufficiently close to the metal-centered $^5D_4$ excited state of the terbium ion (within about 410 cm$^{-1}$ or about 2%) so as to produce significant oxygen sensitivity. In contrast, the europium ion has a $^5D_1$ excited state at about 526 nm (19,010 cm$^{-1}$) and a $^5D_0$ excited state at about 570 nm (17,540 cm$^{-1}$). The excited state of the Schiff base differs by more than about 20 nm (800 cm$^{-1}$ or about 4%) from either of the $^5D_1$ or $^5D_0$ excited states of the europium ion and it is found that the europium complex is not oxygen sensitive. When the excited ligand state and excited lanthanide ion state are close enough in energy, the complex has oxygen sensitivity. By combining the europium ion with another ligand having an excited ligand energy state sufficiently close to the europium excited state, a europium complex can be made which is oxygen sensitive.

This invention also includes methods for improving the oxygen sensitivity of the lanthanide complexes of this invention. A first process consists of reacting the ligand with a strong base, such as sodium or ammonium hydroxide, to deprotonate the ligand and thus form sites for binding with the metal lanthanide ion. Preferably, the metal lanthanide ion is then added to a solution of the ligand and hydroxide whereby the hydroxide groups form additional ligands to the lanthanide ion. It is believed that the hydroxide groups may coordinate with more than one lanthanide ion and thus act as bridging elements to form a multi-metal ion complex, particularly with the Schiff base ligands. The hydroxide is preferably used at a hydroxide:ligand ratio of 1:1, which results in both deprotonation of the ligand and may result in coordination by hydroxide ligands when the metal ion is added to the solution. Use of a substantially higher concentration of hydroxide is not preferred because it may cause a lanthanide hydroxide to precipitate out A second preferred process for making the lanthanide complex consists of a purification step wherein non-oxygen sensitive byproducts are removed. The purification step consists of dissolving the lanthanide complex in a suitable organic solvent, such as chloroform or ethanol, filtering off the insoluble residue (of less oxygen sensitive byproducts), and reprecipitating the compound to produce a more oxygen sensitive complex.

The following two examples set forth specific embodiments of the processes for preparing a Schiff base terbium complex and a $\beta$-diketone terbium complex. Terbium complexes with other preferred Schiff base ligands can be made according to the synthesis described in Example 1 with the substitution of suitable starting materials for the selected ligand.

EXAMPLE 1

Synthesis of Tb(SALAPPD), a Schiff base complex of Tb +3

The ligand is synthesized by adding 18 mmoles (3.0 g) of (1S, 2S)-(+)-2-aminophenyl-1,3-propanediol to a solution of 18 mmoles (2.2 g) of salicylaldehyde in 60 ml of absolute ethanol. This solution is placed in an ultrasonic bath at room temperature until the diol has dissolved and a yellow precipitate (SALAPPD) has formed. The solvent is removed by vacuum filtration. The ligand is recrystallized from 175 ml of hot absolute ethanol. The complex is prepared by dissolving 5.5 mmoles (1.50 g) of SALAPPD in 50 ml of 95% ethanol. 2.8 ml of 2 M NaOH in aqueous solution are added, and the solution is stirred for several minutes. 1.84 mmoles (0.69 g) of $TbCl_3.6H_2O$ are dissolved in 10 ml of 50% ethanol and added to the ligand solution. The yellow precipitate which forms is filtered from the solution and placed in a vacuum desiccator overnight to dry. The dry product is crushed into a powder and dissolved in 10 ml of dry chloroform. After filtration, the solvent is removed by evaporation or under vacuum. The purified product is crushed and desiccated until use.

EXAMPLE 2

Synthesis of Tb(TTFA) into a powder, a $\beta$-diketone complex of Tb +3

9 mmoles (2.0 g) of thenoyltrifluoroacetone (TTFA) and 3 mmoles (1.12 g) of $TbCl_3.6H_2O$ are dissolved in 50 ml of boiling distilled water. 1M aqueous NaOH is added dropwise until formation of the yellow product is complete. The solution remains acidic. After removal of the solvent by filtration, the product is air dried. The metal complex is purified by dissolving in 100 ml of hot absolute ethanol and filtering. Water is added to the ethanol solution to force the complex out of solution. The final product is removed from solution by filtration and the residual solvent is removed by evaporation or under vacuum. The purified product is desiccated until used.

In a preferred embodiment, the oxygen sensor of this invention consists of an oxygen-quenchable lanthanide complex dispersed as a solid solution in a polymeric matrix. The polymer is substantially transparent both to the excitation wavelength and the emission wavelength of the lanthanide complex. The polymeric matrix is permeable to oxygen so as to transfer oxygen from the external fluid (liquid or gas) sample to the lanthanide complex. For example, suitable polymeric materials include poly(styrene), poly(styrene)/divinylbenzene, poly(methylmethacrylate), and silicone elastomers. Poly(methylmethacrylate) is preferred where the excitation wavelength is in the ultraviolet region, because this polymer is substantially optically transparent to and will not degrade in the presence of UV radiation. A suitable poly(methylmethacrylate) is sold by Polysciences, Inc. of Warrington, Pa, having an intrinsic viscosity of 0.2 and an approximate molecular weight of 33,000. Silicone elastomers containing the terbium complexes are preferably used in a nonaqueous environment because the luminescence response exhibits some degradation in an aqueous environment. However, the terbium complex adsorbed on poly(styrene)/divinylbenzene beads and dispersed in a silicone elastomer produces a stable sensor body which will not substantially degrade in an aqueous environment.

The oxygen sensitivity of a sensor consisting of an oxygen-quenchable lanthanide complex dispersed in a solid polymeric matrix depends upon three factors: (1) the complex; (2) the matrix; and (3) the concentration of the complex in the matrix. Furthermore, the desired sensitivity of the oxygen sensor depends upon the level of oxygen to be measured. One method of evaluating the sensitivity of $O_2$ sensors is to determine the luminescence ratio of a nitrogen saturated sample compared to a sample equilibrated with a known level (usually 20%) of oxygen. This ratio can be used to determine the utility of a test complex at a given concentration in a specific matrix. In an in vivo medical application where the $O_2$ concentration is determined in a substantially aqueous solution, this ratio may range from about 2 to about 15. The previously described preferred Schiff base ligands based on salicylaldehyde or substituted salicylaldehydes fall within this range. The following $\beta$-diketone ligands create terbium complexes which when dispersed in a silicone elastomer also fall within this range: benzoylacetone; trifluoroacetylacetone; and furylbutanedione. The terbium complex of thenoyltrifluoroacetone dispersed in a silicone matrix has a very high intensity ratio (i.e., about 35) which makes it suitable for use at very low oxygen concentrations, below that normally encountered in a medical application. However, by dispersing this complex in poly(methylmethacrylate), which takes up less oxygen than silicone, a less sensitive oxygen sensor can be made. In contrast, other $\beta$-diketone terbium complexes have an intensity ratio of less than two when dispersed in a silicone matrix, e.g., dibenzoylmethane or trifluorophenylbutanedione, and are thus suitable for use at much higher oxygen concentrations.

In another aspect, this invention consists of a combination measuring and reference sensor containing both quenchable and nonquenchable luminescent materials. A first measuring material has a luminescence in a first wavelength range which is quenched by the analyte. A second reference material is disposed adjacent to the first material and has a luminescence in a second wavelength range different from the first wavelength range and which is not substantially quenched by the analyte. The luminescence from the first material constitutes a measuring signal which is inversely proportional to the concentration of the analyte exposed to the sensor. The luminescence from the second material constitutes a reference signal which is not effected by the presence of the analyte and which is used to continuously monitor the source radiation used to excite the first and second materials and the losses in the sensor system. Because the luminescence from the first and second materials are in different wavelength ranges, a single optical fiber can be used for conducting both of these signals and filter means are used for discriminating the same.

By way of example, the oxygen-quenchable Tb(SALAPPD) complex as a first material and the nonoxygen-quenchable Eu(SALAPPD) complex as the second material are disposed in solid solution in a polymeric matrix. The matrix is disposed at the distal tip of a single optical fiber. The fiber tip is placed in the sample, and the $O_2$ gas in the sample permeates the polymeric matrix. An incident energy signal for exciting both the first and second materials is sent down the fiber and causes the first and second materials to luminesce. The luminescence from the oxygen sensitive terbium complex is reduced in proportion to the concentration of oxygen present whereas the luminescence from the europium complex is proportional to the incident signal, minus any system losses. The luminescence signals from the terbium and europium complexes return down the fiber to its proximal end where they are discriminated by means of filters and sent to separate detectors for measuring the same. The combination sensor will be further described hereinafter with respect to a specific embodiment of a blood gas sensor.

In a third aspect of this invention, a low-noise, phosphorescent analyte sensor is provided. The sensor employs an analyte-quenchable luminescent material having a relatively long-lived luminescence or phosphorescence. A delayed detection of that phosphorescence, after the exciting source energy and any broadband background luminescence has ceased, produces a low-noise output signal. The low-noise sensor will be described by means of a specific embodiment consisting of a fiber optic oxygen sensor probe for in vivo monitoring of the oxygen concentration within a body cavity, such as the blood vessels. The probe will further encompass the first and second aspects of this invention and thus include an oxygen-quenchable luminescent lanthanide complex as the measuring material in combination with a nonoxygen-quenchable luminescent lanthanide complex as a reference material. Both complexes are contained in a polymeric bead disposed at the distal end of a single optical fiber. Both complexes exhibit relatively long-lived luminescence or phosphorescence such that by pulsing an excitation source and selectively coupling and decoupling the detector so that the detector is on only when the excitation source is off and any short-lived background luminscence has ceased, the output signal consists only of the phosphorescent measuring and reference signals.

In order to produce a low-noise measuring and reference signal, the measuring and reference complexes must generate a long-lived luminescence or phosphorescence. As used herein, the term phosphorescence means a relatively long-lived luminescence which exists after the excitation energy has ended, as opposed to short-lived fluorescence which usually ceases in less than $10^{-7}$ seconds when the exciting energy is turned off. Preferably, the phosphorescence has a life-time of at least about $10^{-5}$ seconds, and more preferably greater than about $10^{-4}$ seconds.

The preferred in vivo oxygen probe and associated apparatus are shown in FIGS. 1-5. The sensor includes an optical fiber 10 having a proximal end 12 and a distal end 14. Disposed at the distal end of the fiber is a sensor body 16 consisting of a solid body of a polymeric material containing both the measuring oxygen-quenchable luminescent lanthanide complex and the reference nonoxygen-quenchable luminescent lanthanide complex. Preferably, the polymeric material is poly(methylmethacrylate) which will adhere directly to the fiber. Alternatively, the lanthanide complexes may be adsorbed on porous poly(styrene)/divinylbenzene beads which are dispersed in a silicone elastomer that is directly adhered to the distal end of the fiber, or the porous poly(styrene)/divinylbenzene beads on which the lanthanide complexes are adsorbed may be encapsulated by a porous polyethylene or Teflon sheath, such as Celgard or Goretex, and the sheath attached to the fiber with adhesive.

The sensor body 16 is preferably formed by dipping the distal end of the fiber in a solution of the polymeric matrix material, the oxygen-quenchable lanthanide complex, and the nonoxygen-quenchable reference complex, and allowing the solvent to evaporate. A small polymeric bead of about 50-100 micrometers can thus be formed on a 100 micrometer diameter fiber, as shown in FIG. 2.

For example, the dipping solution may comprise about 2.5 g of the Tb(SALAPPD) complex, 0.5 g of the Eu(SALAPPD) complex, and 97.0 g of poly(methylmethacrylate) dissolved in ethyl acetate at about 20% solids. The resulting body will thus have about 2.5% by weight of the terbium complex and 0.5% by weight of the europium complex.

To the left of the fiber in FIG. 1, a radiation source, detectors, and various optical and electronic elements are provided. A pulsed incoherent energy source 40, such as a mercury or xenon discharge lamp, produces broadband radiation which is partially collected and collimated by a lens 42. The collimated signal from lens 42 is received by a narrowband filter 44 which rejects nearly all of the radiation from the source except for a narrow segment which includes at least part of a predetermined wavelength range at which the measuring and reference luminescent materials are excited. This narrowband signal is imaged onto the face of the proximal end 12 of the fiber by a second lens 46. The radiation travels to the distal end of the fiber where it passes directly into the gas-absorbing region defined by the body 16. The luminescent radiation generated in the body by the measuring and reference materials is transmitted back through the fiber and lens 46 through a half-silvered mirror 48 to a beam splitter 50 which separates the output radiation into two equal components. The first output component is sent through a filter 52 which passes radiation in the wavelength range of the luminescence from the measuring material and then onto the active area of a first detector 54. The second component of the output signal passes through a filter 55 which passes radiation in the wavelength range of the luminescence of the reference material and finally onto the active area of a second detector 56. The intensities of the luminescence from the measuring and reference materials are thus separately measured and sent to a microprocessor 58 for calculating the value of the oxygen concentration in the blood.

In order to eliminate background noise from the output luminescence signal, a gating means 60 is provided between the source means 40 and the detectors 54 and 56, to selectively couple and decouple the detectors. For example, at a time $t_0$ the gating means sends an electronic signal to the source causing the source to emit a pulse of radiation. At the same time $t_0$ the gating means sends electronic signals to each of the detectors disabling the same. At a predetermined time period after the source means is shut off and any short-lived background luminescence has ceased, the gating means sends a signal to each of the detectors activating the same. In this manner, only the long-lived luminescence from the measuring and reference materials is detected. Other types of gating means may also be used.

The fiber optic sensor is inserted into a blood vessel or body cavity via a carrier means. By carrier means it is meant a flexible or rigid tubular member for insertion into the body vessels or cavities, such as a catheter, needle or probe. A suitable carrier means is shown in FIGS. 3-5, consisting of a catheter formed from an elongate flexible body 102 and which may, for example, be extruded from an appropriate plastic material such as polyurethane or polyvinyl chloride. A 3.5 French catheter, having an outer diameter of 0.045 inch, may be used. The body 102 has a first smaller lumen 104 in which a single optical fiber 110 of the sensor is enclosed, and a second larger lumen 106 for fluid infusion.

The proximal end of the catheter includes a molded fitting 120 which is secured to the catheter body 102. Projecting from the proximal end of the fitting 120 are a pair of flexible tubes 122, 124. The tube 122 is adapted to receive the optical fiber 110, which extends through the fitting 120. The proximal end of the tube 122 is provided with a connector 126 which is connected to the proximal end of the optical fiber 110. Connector 126 is adapted to be mounted with respect to a source of radiant energy, such as a flash lamp (illustrated diagramatically at 127) so that the proximal end of the optical fiber 110 may receive the radiant energy and conduct it along its length to the distal end of the fiber.

The smaller lumen 104 is skived back from the distal end of the catheter body 102, so that the larger lumen 106 extends distally beyond the distal end of the smaller lumen. The optical fiber 110 and sensor body 116 extend slightly beyond the distal end of the smaller lumen so that the sensor tip 116 will be in contact with the blood. The longer wall of the larger lumen helps protect the exposed sensor tip and fiber from breakage. Epoxy 117 is disposed around the fiber between the fiber and smaller lumen adjacent the distal end of the fiber to secure the fiber and sensor in place and to seal the distal end of the smaller lumen.

The other tube 124 at the proximal end of the catheter communicates through the fitting 120 with the larger lumen 106 and preferably is provided with a conventional luer connector 128. The pathway thus defined between the luer connector 128, tube 124, and larger lumen 106 which is open at its distal end permits communication with the region of the patient's blood vessel or body cavity where the distal end of the catheter is located It provides a passageway for fluids to flow both to and from the patient's blood vessel and also provides a means for making pressure measurements.

More particularly, the preferred in vivo probe for measuring the oxygen concentration of the blood will now be described having a sensor body consisting of the Tb(SALAPPD) complex and Eu(SALAPPD) complex as the measuring and reference materials, respectively, dispersed in a poly(methylmethacrylate) matrix. Both complexes have a maximum excitation efficiency at 350–360 nm, and thus a filter 44 having a bandpass of 350–400 nm is selected. The 547 nm emission peak for the terbium complex, and the 617 nm emission peak for the europium complex, are selected for maximum intensity and minimum overlap A 546±10 nm filter 52 is used for the terbium peak and a 620±10 nm filter 55 is used for the europium peak. The output from the 546 nm filter is substantially 100% terbium. The with the remaining 5% coming from a 623 nm emission peak of terbium. Photomultiplier tubes are used as the detectors 54 and 56.

The optical fiber is a commercially available silica fiber sold under the trademark Superguide FH, by Fiberguide Industries, Sterling, N.J. The pulsed source is a xenon flash lamp, EG&G 198 FX, sold by E. G. & G., Salem, Mass., having a pulse width (full width at half maximum amplitude) of 10 microseconds. The Tb(SALAPPD) complex disposed in poly(methylmethacrylate) has an unquenched lifetime of approximately 1300 microseconds, and the Eu(SALAPPD) complex disposed in poly(methylmethacrylate) has an unquenched lifetime of approximately 550 microseconds. The detectors are gated on about 100 microseconds after the source is shut off which is sufficient for substantially all of the excitation energy and any short-lived luminescence generated in the system to cease.

A modified Stern-Volmer relationship is used to determine the partial pressure of oxygen from the measuring and reference signals. As shown in FIG. 6, the Stern-Volmer relation at 546±10 nm is a relatively steep line indicating the oxygen sensitivity of the terbium complex. The relationship is defined by the equation:

$$\frac{I_0}{I} = 1 + K_{546} PO_2 \quad (I)$$

where $I_0$ is the luminescence intensity at 546± 10 nm with no oxygen present, I is the luminescence intensity at 546±10 nm in the presence of oxygen, and $K_{546}$ is the Stern-Volmer constant at 546±10 nm and is equal to the slope of the line in FIG. 6.

Figure 7:
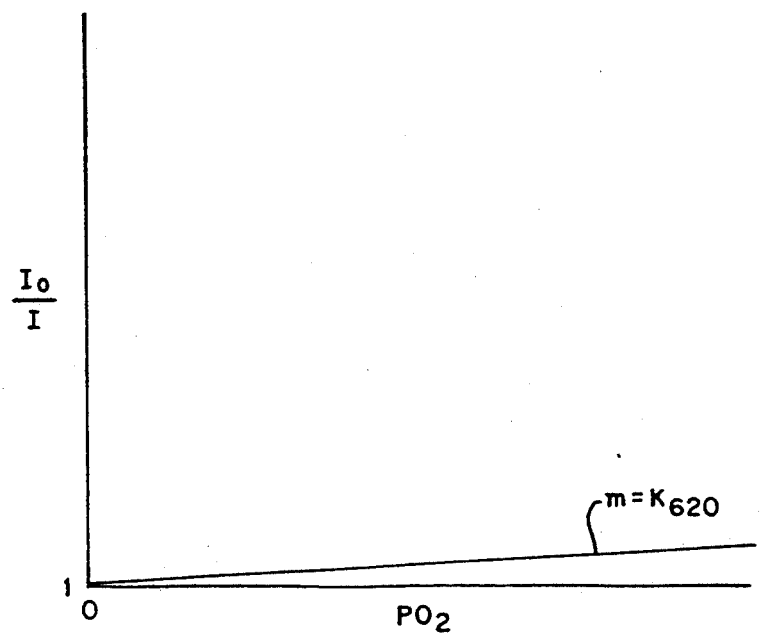
FIG. 7 is a graphical illustration of the Stern-Volmer relation for an oxygen insensitive europium complex.

As shown in FIG. 7, the Stern-Volmer relation at 620±10 nm is almost a horizontal line representing a very slight oxygen response attributable to the weak terbium luminescence. The relation has the formula:

$$\frac{I_0}{I} = 1 + K_{620} PO_2 \quad (II)$$

where $I_0$ is a luminescence intensity at 620±10 nm with no oxygen present, I is the luminescence intensity at $620\pm10$ nm with oxygen present, and $K_{620}$ is the slope of the line in FIG. 7.

Combining formulas I and II results in the following relation:

$$\frac{R}{R_o} = \frac{1 + K_{546}PO_2}{1 + K_{620}PO_2} \quad \text{(III)}$$

where $R_o$ is the luminescence intensity at $620\pm10$ nm divided by the luminescence intensity at $546\pm10$ nm with no oxygen present, and R is the intensity at $620\pm10$ nm divided by the intensity at $546\pm10$ nm in the presence of oxygen. Thus, by inserting into formula III the intensity values measured for the terbium and europium complexes at 546 and 620 nm, respectively, and knowing the constants $K_{546}$ and $K_{620}$ determined from initial calibration with known concentrations of $O_2$, the partial pressure of oxygen in the sample can be determined. The use of the reference signal at 620 nm provides continuous monitoring of the level of the incident signal and the losses in the system during use.

The Tb(SALAPDD) complex disposed in a poly(methylmethacrylate) matrix has been found to have a Stern-Volmer constant $K_{546}$ of greater than about $9\times10^{-3}$ mm $Hg^{-1}$. The sensitivity of the Tb(TTFA) complex in the same polymeric matrix is even greater. In selecting an oxygen-quenchable lanthanide complex for a specific application, one must balance the sensitivity against the concentration of oxygen to be measured to ensure that a measurable intensity results. The normal ranges of oxygen concentration in the blood are for arterial blood from about 80–100 mm Hg, for venous blood from about 35–45 mm Hg, and for neonatal blood in the umbilical vessel from about 60–80 mm Hg. The preferred sensor, consisting of about 2.5% by weight of the Tb(SALAPPD) complex in poly(methylmethacrylate), allows a determination of $PO_2$ within all three normal blood oxygen ranges to an accuracy of within about $\pm5\%$.

The following example describes a specific test conducted for determining the oxygen sensitivity of a sensor based on the Tb(SALAPPD) complex and Eu(SALAPPD) complex as the measuring and reference materials, respectively.

EXAMPLE 3

Sensitivity of a preferred oxygen sensor

The utility of the oxygen sensor was demonstrated by measuring the intensity of the measuring (Tb[SALAPPD]) and reference (Eu[SALAPPD]) materials combined in a polymer matrix as a function of oxygen partial pressure. Quartz slides (approximately $0.8\times2.8\times0.2$ mm) were coated by immersion in an ethyl acetate solution containing 20% poly(methylmethacrylate), 0.40% Tb(SALAPPD) and 0.05% Eu(SALAPPD) by weight. After removal of the solvent by evaporation, the polymer contained about 2% Tb(SALAPPD) and about 0.25% Eu(SALAPPD).

The samples were mounted in a water-filled quartz cuvette in the sample chamber of a commercial spectrofluorimeter (Fluorolog Model 111, SPEX Industries, Metuchen, NJ). The instrument was equipped with a pulsed light source and gated detection optics (Model 1934C Phosphorimeter; SPEX Industries; Metuchen, NJ). Gas was introduced into the chamber via a Teflon needle, and the oxygen concentration in a nitrogen carrier gas was fixed by a micro-processor controlled gas mixer (PGM-3 Precision Gas Mixer, Linde division of Union Carbide, Somerset, NJ). The oxygen concentration in the gas stream had previously been calibrated by mass spectroscopy. The temperature of the sample was controlled to $37°\pm0.05°$ C.

The sample was excited at $350\pm15$ nm. The intensity of the measuring signal (Tb[SALAPPD]) was measured at $547\pm0.9$ nm. The reference (Eu[SALAPPD]) intensity was measured at $617\pm0.9$ nm. $R_o$ is calculated from the reference to measuring intensity ratio under nitrogen saturated conditions and has a value of 0.422. R is the reference to measuring intensity ratio measured at known oxygen partial pressures.

Figure 8:
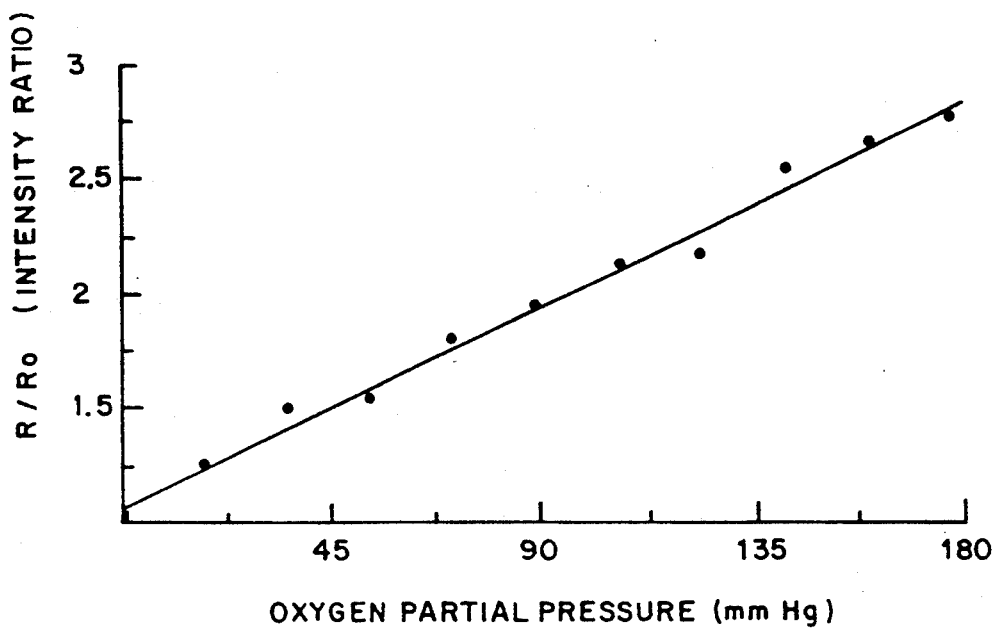
FIG. 8 is a graphical illustration of a calibration curve for a combination measuring and reference sensor.

The data in FIG. 8 shows the oxygen response $(R/R_o)$ versus oxygen partial pressure. The data are clearly linear and follow the behavior described previously at formula III as:

$$\frac{R}{R_o} = \frac{1 + K_{Tb}PO_2}{1 + K_{Eu}PO_2} \quad \text{(IV)}$$

where $K_{Tb}$ is the slope of the Stern-Volmer plot measured at $547\pm0.9$ nm and $K_{Eu}$ is the slope of the Stern-Volmer plot measured at $617\pm0.9$ nm. This equation will yield a linear plot of $R/R_o$ versus $PO_2$ if $1>>KEuPO_2$. This condition is met under the conditions of this experiment.

From the slopes of the lines, the value of $K_{Tb}$ is 0.00991 mm $Hg^{-1}$. Rearranging the previous equation IV and eliminating the denominator (which is approximately one):

$$PO_2 \text{ in mmHg} = \frac{R/R_o - 1}{K_{Tb}} \quad \text{(V)}$$

by inserting the measured intensities, $PO_2$ is calculated from:

$$PO_2 = (239 * R) - 101 \text{ mm Hg.} \quad \text{(VI)}$$

Figure 9:
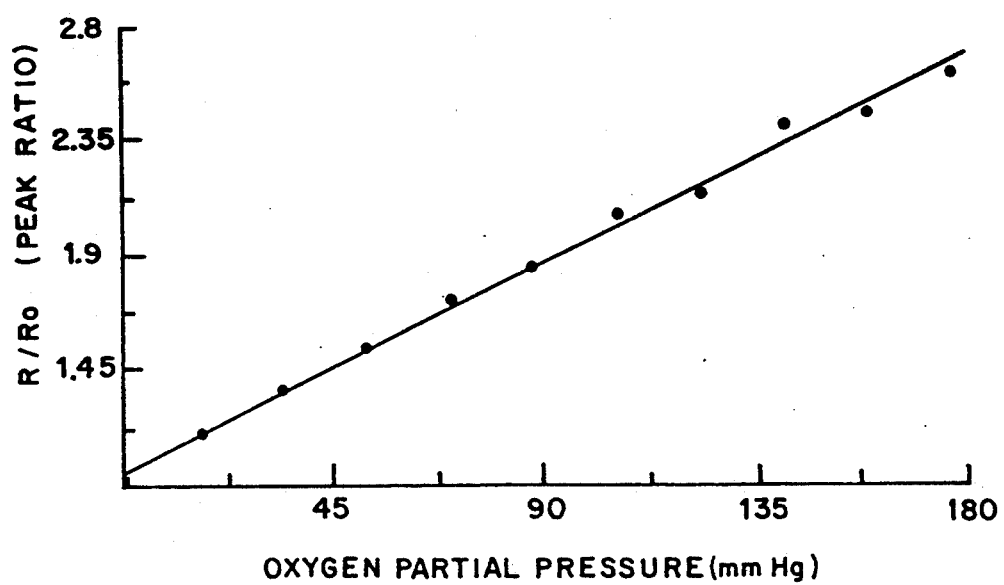
FIG. 9 is a graphical illustration showing the close correspondance between calculated and theoretical values of $PO_2$ for the combination sensor.

FIG. 9 shows that the plot of calculated $PO_2$ values, determined by substituting experimental values of R into equation VI, versus theoretical $PO_2$ values, derived from the settings on the gas mixer, has a slope of 1.00 with a correlation coefficient of 0.997. Thus, $PO_2$ determined by the sensor/reference system described above is in very close agreement with the expected values.

While certain preferred embodiments of the invention have hereinbefore been described, it will be appreciated that variations thereof will be perceived by those skilled in the art, which variations are nevertheless within the scope of the invention as defined by the claims appended hereto.

What is claimed is:

1. An oxygen gas sensor comprising an oxygen-quenchable luminescent lanthanide complex and detector means operatively connected to said complex for detecting oxygen-quenching of said complex, said complex being of at least one lanthanide ion which emits a narrow-line luminescence when excited to a predetermined energy state and at least one ligand having an excited ligand energy state from which it transfers energy to said lanthanide ion to cause said ion to luminesce, said excited ligand energy state being substantially equal to said predetermined energy state so that said lanthanide ion and ligand form a resonant pair between which energy is rapidly transferred back and forth such that the presence of oxygen substantially interferes with the transfer of energy between the resonant pair of quenches said excited ligand energy state.

2. The sensor of claim 5, wherein said predetermined energy state and said excited ligand energy state differ by no more than about 410 cm$^{-1}$.

3. The sensor of claim 1, wherein said excited ligand energy state differs by no more than about two percent of said predetermined energy state.

4. An oxygen gas sensor comprising an oxygen-quenchable luminescent lanthanide complex in a solid matrix and detector means operatively connected to said complex for detecting oxygen-quenching of said complex, said lanthanide complex comprising at least one lanthanide ion which emits a narrow-line luminescence when excited to a predetermined energy state and at least one ligand having an excited ligand energy state from which it transfers energy to said lanthanide ion to cause said ion to luminesce, said excited ligand energy state being substantially equal to said predetermined energy state so that said lanthanide ion and ligand from a resonant pair between which energy is rapidly transferred back and forth such that the presence of oxygen substantially interferes with the transfer of energy between the resonant pair of quenches said excited ligand energy state.

5. The sensor of claim 4, wherein said solid matrix is a polymeric matrix.

6. The sensor of claim 5, wherein said lanthanide complex is in solid solution in said polymeric matrix.

7. An oxygen gas sensor comprising an oxygen-quenchable luminescent lanthanide complex and detector means operatively connected to said complex for detecting oxygen-quenching of said complex, said complex being of at least one lanthanide ion which emits a narrow-line luminescence when excited to a predetermined energy state and at least one ligand which is excited by absorbing energy at a wavelength above 300 nm to an excited ligand energy state from which it transfers energy to said lanthanide ion to cause said ion to luminesce.

8. An oxygen gas sensor comprising an oxygen-quenchable luminescent multi-metal ion lanthanide complex and detector means operatively connected to said complex for detecting oxygen-quenching of said complex, said complex having a plurality of lanthanide metal ions and a plurality of ligands wherein at least one of said ligands is complexed with more than one of said lanthanide ions.

9. The sensor of claim 8, wherein said ligands include hydroxide ligands.

10. The sensor of claim 8, wherein said ligands are selected from the group consisting of Schiff base and $\beta$-diketone ligands.

11. The sensor of claim 10, wherein said complex includes terbium ions and at least one Schiff base ligand completed with more than one terbium ion.

12. The sensor of claim 11, wherein said complex includes at least three terbium ions and at least three Schiff base ligands.

13. The sensor of claim 12, wherein said ligands include hydroxide ligands.

14. An oxygen gas sensor comprising an oxygen-quenchable luminescent lanthanide complex and detector means operatively connected to said complex for detecting oxygen-quenching of said complex, said complex comprising at least one ligand which can exit in an excited energy state after absorbing incident radiation, said excited energy state being elevated above an unexcited energy state for the ligand by an amount substantially equal to the energy difference between an unexcited energy state for the lanthanide ion and an energy state from which the lanthanide ion luminesces, wherein the lanthanide ion is caused to luminesce after the ligand has been promoted to the excited energy state, by incident radiation, and the intensity of said luminescence is quenched, at least in part, by the presence of oxygen.

15. The sensor of claim 14, wherein the excited energy state for the ligand is raised above its unexcited energy state by an amount within 4% of the energy state from which the lanthanide ion luminesces.

16. The sensor of claim 14, wherein the excited energy state for the ligand is raised above its unexcited energy state by an amount within 410 cm$^{-1}$ of the energy state from which the lanthanide ion luminesces.

* * * * *

UNITED STATES PATENT AND TRADEMARK OFFICE
CERTIFICATE OF CORRECTION

PATENT NO. : 5,190,729
DATED : March 2, 1993
INVENTOR(S) : Hauenstein et al.

It is certified that error appears in the above-indentified patent and that said Letters Patent is hereby corrected as shown below:

Col. 2, line 9 — delete "Lěbbers" and substitute therefore. -- Lübbers --.

Col. 4, line 54 — delete "Ianthanide" and substitute therefore -- lanthanide --.

Col. 8, line 36, — delete "propanesalicylald diol" and substitute therefore -- propanediol --.

Col. 14, line 5 — after "located" insert -- . --.

Col. 14, line 23 — after "The" insert -- output of the 620nm filter is about 95% europium, --.

Col. 14, line 50 — equation should read:
$$\frac{I_o}{I} = 1 + K_{546} PO_2 \quad (I)$$

Col. 17, line 3 — delete "of" and substitute therefore -- or --.

Col. 17, line 4 — delete "5" and substitute therefore -- 1 --.

Col. 17, line 21 — delete "from" and substitute therefore -- form --.

Col. 17, line 25 — delete "of" and substitute therefore -- or --.

Signed and Sealed this

First Day of March, 1994

BRUCE LEHMAN

*Attest:*

*Attesting Officer*  *Commissioner of Patents and Trademarks*